United States Patent
Bojarczuk et al.

(10) Patent No.: US 9,417,126 B2
(45) Date of Patent: Aug. 16, 2016

(54) SPECTROMETER INSERT FOR MEASURING TEMPERATURE-DEPENDENT OPTICAL PROPERTIES

(71) Applicant: International Business Machines Corporation, Armonk, NY (US)

(72) Inventors: Nestor A. Bojarczuk, Poughkeepsie, NY (US); Talia S. Gershon, White Plains, NY (US); Teodor K. Todorov, Yorktown Heights, NY (US); Theodore G. van Kessel, Millbrook, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/317,193

(22) Filed: Jun. 27, 2014

(65) Prior Publication Data

US 2015/0377702 A1 Dec. 31, 2015

(51) Int. Cl.
*G01J 3/46* (2006.01)
*G01J 3/02* (2006.01)
*G01N 21/03* (2006.01)
*G01N 21/3563* (2014.01)

(52) U.S. Cl.
CPC ............ *G01J 3/0286* (2013.01); *G01J 3/0205* (2013.01); *G01N 21/0332* (2013.01); *G01N 21/3563* (2013.01); *G01N 2021/3568* (2013.01)

(58) Field of Classification Search
CPC ................ G01J 3/46; G01J 3/50; G01J 3/02; G01J 3/524; G01J 3/51
USPC ........................................................ 356/402
See application file for complete search history.

(56) References Cited

U.S. PATENT DOCUMENTS

| | | |
|---|---|---|
| 4,716,293 A | 12/1987 | Harrick |
| 5,118,200 A | 6/1992 | Kirillov et al. |
| 5,166,755 A | 11/1992 | Gat |
| 5,388,909 A | 2/1995 | Johnson et al. |
| 5,703,689 A | 12/1997 | Powell |
| 5,801,384 A * | 9/1998 | Kirchhevel .................... 250/345 |
| 6,178,822 B1 * | 1/2001 | Manning .......................... 73/668 |
| 6,679,946 B1 | 1/2004 | Jackson et al. |
| 6,891,124 B2 | 5/2005 | Denton et al. |
| 7,283,218 B2 | 10/2007 | Zettler |
| 7,310,153 B2 | 12/2007 | Kiesel et al. |
| 7,976,216 B2 | 7/2011 | Timans |
| 2004/0014234 A1 * | 1/2004 | Uchihara et al. ............... 436/155 |
| 2004/0066895 A1 * | 4/2004 | Hoshino .......................... 378/86 |
| 2004/0108453 A1 * | 6/2004 | Kobayashi et al. ............ 250/281 |
| 2010/0019140 A1 * | 1/2010 | Amirav et al. ................. 250/282 |
| 2012/0104269 A1 * | 5/2012 | Clark et al. .................... 250/375 |
| 2013/0207000 A1 * | 8/2013 | Gunther et al. ............ 250/396 R |
| 2013/0320206 A1 * | 12/2013 | Christy ......................... 250/288 |
| 2014/0176946 A1 * | 6/2014 | Matsumoto et al. ........... 356/402 |

* cited by examiner

*Primary Examiner* — Tarifur Chowdhury
*Assistant Examiner* — Md M Rahman
(74) *Attorney, Agent, or Firm* — Vazken Alexanian; Michael J. Chang, LLC

(57) ABSTRACT

In one aspect, a spectrometer insert is provided. The spectrometer insert includes: an enclosed housing; a first transparent window on a first side of the enclosed housing; a second transparent window on a second side of the enclosed housing, wherein the first side and the second side are opposing sides of the enclosed housing; and a sample mounting and heating assembly positioned within an interior cavity of the enclosed housing in between, and in line of sight of, the first transparent window and the second transparent window. A method for using the spectrometer insert to locally heat a sample so as to measure temperature-dependent optical properties of the sample is also provided.

5 Claims, 5 Drawing Sheets

SPECTROMETER INSERT FOR MEASURING TEMPERATURE-DEPENDENT OPTICAL PROPERTIES

FIELD OF THE INVENTION

The present invention relates to spectrometer-based optical analysis of a (e.g., semiconductor) sample and more particularly, to a spectrometer insert and use thereof for locally heating the sample to measure temperature-dependent optical properties of the sample.

BACKGROUND OF THE INVENTION

The optical properties of most materials, especially semiconductors, depend heavily on the temperature at which measurements are taken. Most semiconductors display smaller band gaps at high temperatures and larger band gaps at low temperatures. In order to design and model optoelectronic materials for high-temperature applications, the temperature-dependence of absorption and transmission must be known.

Benchtop spectrometers operate at room temperature and can provide valuable information about absorption and transmission through a sample. Direct heating of a sample in a spectrometer to high temperatures (for example above 600° C.) without appropriate insulation is not advised as the heat is likely to transfer to the spectrometer itself and damage the tool.

Therefore, techniques for measuring the properties of a semiconductor while heating would be desirable.

SUMMARY OF THE INVENTION

The present invention provides a spectrometer insert and techniques for use thereof for locally heating a sample to measure temperature-dependent optical properties of the sample. In one aspect of the invention, a spectrometer insert is provided. The spectrometer insert includes: an enclosed housing; a first transparent window on a first side of the enclosed housing; a second transparent window on a second side of the enclosed housing, wherein the first side and the second side are opposing sides of the enclosed housing; and a sample mounting and heating assembly positioned within an interior cavity of the enclosed housing in between, and in line of sight of, the first transparent window and the second transparent window.

In another aspect of the invention, a method for analyzing temperature-dependent optical properties of a sample is provided. The method includes the steps of: mounting the sample in a spectrometer insert, wherein the spectrometer insert includes i) an enclosed housing, ii) a first transparent window on a first side of the enclosed housing, iii) a second transparent window on a second side of the enclosed housing, wherein the first side and the second side are opposing sides of the enclosed housing, and iv) a sample mounting and heating assembly, to which the sample is mounted, positioned within an interior cavity of the enclosed housing in between, and in line of sight of, the first transparent window and the second transparent window; placing the spectrometer insert in a spectrometer such that the spectrometer insert is between a light source of the spectrometer and a photodetector of the spectrometer, and the first transparent window and second transparent window are within line of sight of the light source and the photodetector; creating a vacuum within the enclosed housing; heating the sample to one or more temperatures; transmitting light from the light source, through the enclosed housing via the first transparent window and the second transparent window, to the photodetector; and collecting data from the photodetector relating to optical properties of the sample at the one or more temperatures.

A more complete understanding of the present invention, as well as further features and advantages of the present invention, will be obtained by reference to the following detailed description and drawings.

DETAILED DESCRIPTION OF PREFERRED EMBODIMENTS

As provided above, it is important to know the temperature-dependent properties of a semiconductor especially when the semiconductor is going to be used in high-temperature applications. However, conventional spectrometers do not permit the heating of samples to high temperatures. Advantageously, provided herein is a spectrometer insert which permits local sample heating while insulating the tool itself from the high-temperatures to which the sample will be exposed, and which also provides a direct pathway of light from the spectrometer source, through the sample, to the detector.

Figure 1:
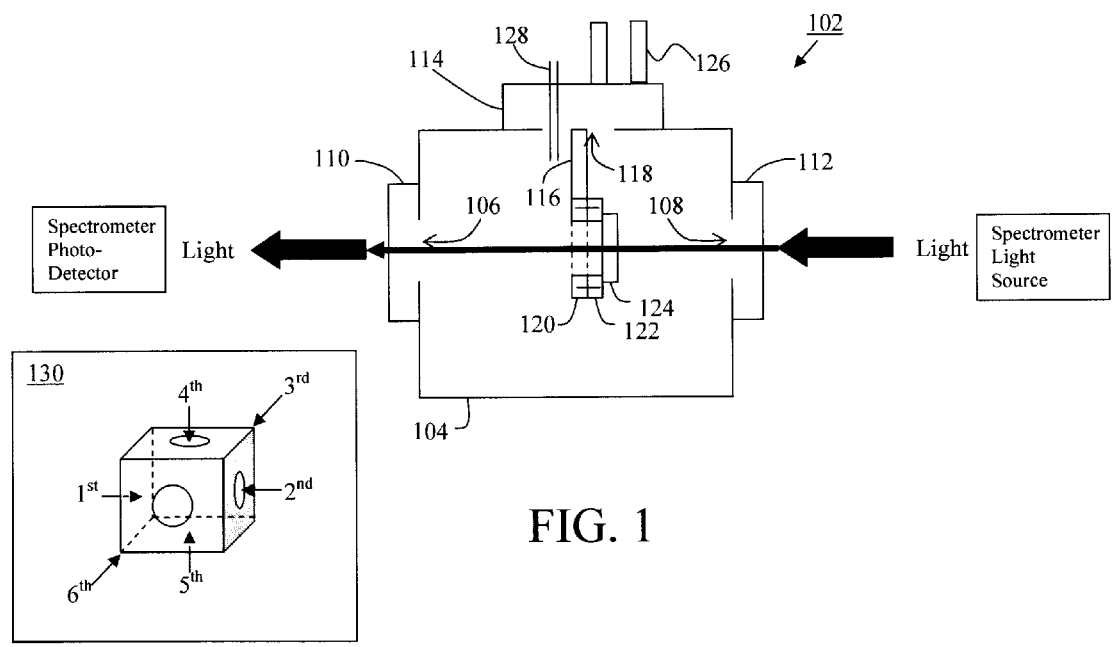
FIG. 1 is a cross-sectional diagram illustrating an exemplary configuration of the present spectrometer insert and its mechanism of operation according to an embodiment of the present invention.

The present techniques are now described in detail by way of reference to FIGS. 1-9. Referring first to FIG. 1, an exemplary configuration of the present spectrometer insert 102 and its mechanism of operation are provided. FIG. 1 provides a cross-sectional view through the center of the insert.

In the example shown in FIG. 1, spectrometer insert 102 includes a hollow, enclosed, cube-shaped housing 104 having a (first) window opening 106 in a first side thereof and a (second) window opening 108 in a second side thereof (which may be two of the generic ports 302 in the cube-shaped housing—see FIG. 3, described below). The first and second sides are opposing sides of the cube-shaped housing 104 such that a spectrometer light beam can pass directly through both window openings 106 and 108 in the housing 104. See FIG. 1. It is notable that spectrometer insert 102 is designed to be inserted into a benchtop spectrometer to achieve temperature-dependent optical measurements.

As will be described in detail below, the present spectrometer insert permits operation under vacuum. Thus each of the window openings 106 and 108 are sealed with an airtight, transparent window 110 and 112, respectively. According to an exemplary embodiment, transparent windows 110 and 112 are formed from a commercially available sapphire or deep-UV quartz material. In the example shown in FIG. 1, the transparent windows 110 and 112 are affixed to an outer surface of the first and second sides of the cube-shaped housing 104 over the (first) window opening 106 and the (second) window opening 108, respectively.

A third side of the cube-shaped housing (not visible in FIG. 1—see insert 130) provides a port for wires to connect a heating element to a power supply (and for an optional thermocouple). The third side of the cube-shaped housing 104 is perpendicular to both the first and second sides of the cube-shaped housing 104.

A sample mounting structure 120 and the heating element 122 (also collectively referred to herein as a sample mounting and heating assembly) are suspended from a fourth side of the cube-shaped housing 104. The fourth side of the cube-shaped housing 104 is perpendicular to both the first and second sides of the cube-shaped housing 104. Suspending the sample holder and heating element from the fourth side of the cube-shaped housing 104 permits a sample to be placed directly in the path of the spectrometer light beam through the window openings 106 and 108. The heating element permits the sample to be locally heated.

More specifically, as shown in FIG. 1, a flange 114 is present on the fourth side of the cube-shaped housing 104. An electrically insulating rod 116, which is attached at a first end thereof to flange 114, passes through opening 118 (which may be one of the generic ports 302—see FIG. 3, described below) in the third side of the cube-shaped housing 104. A second end of electrically insulating rod 116 is attached to a sample mounting structure 120. A heating element 122 is attached to the sample mounting structure 120. A sample on a transparent (e.g. quartz) carrier 124 is placed on the heating element 122. According to an exemplary embodiment, heating wires for connecting the heating element 122 to a power supply, and a thermocouple for measuring sample temperature are provided through the third side of the cube-shaped housing 104. The third side of the cube-shaped housing 104 (not visible in FIG. 1) is perpendicular to the first, second, fourth and fifth sides of the cube-shaped housing 104.

For reference, a three-dimensional depiction of the cube-shaped housing 104 is shown in inset 130 which, by way of example only, illustrates how the various sides (i.e., first, second, third, etc.) of the cube-shaped housing 104 will be referenced throughout the following description. The labeling of a side as a first side, a second side, etc. is purely arbitrary. However, the orientation of a given side of the cube-shaped housing 104 vis-à-vis one or more other sides can be an important consideration in the design. For instance, the transparent window 110 and 112 are to be located on opposite sides of the cube-shaped housing 104 so as to permit the spectrometer light beam to pass through the housing.

In an exemplary embodiment described in detail below, the sample mounting structure 120 and the heating element 122 are both disc-shaped structures having a hole in the center thereof for light-penetration. In such a configuration it may be preferable to configure the sample mounting structure 120 and the heating element 122 to be geometrically matched to one another (e.g., the sample mounting structure 120 and the heating element 122 are configured to have the same sized disc-shaped structure). It is notable however that a variety of different shapes can in fact be employed for the heating element 122. For instance, depending on the size and/or shape of the sample, it may be desirable to instead configure the heating element commensurate in size and shape with the sample (rather than the sample mounting structure 120) to ensure more effective heating of the sample.

In the example shown in FIG. 1, the flange 114 is affixed to an outer surface of the fourth side of the cube-shaped housing 104 over the opening 118. Preferably, attachment of the flange to the cube-shaped housing 104 is configured in such a manner that the flange 114, and with it the sample mounting and heating assembly, can be easily, effectively, and repeatedly inserted and removed from the cube-shaped housing 104. Such action is necessary to be able to mount and change samples within the spectrometer insert. Specifically, the cube-shaped housing 104 is preferably fully sealed so as to be able to permit operation under vacuum (see below). As provided below, vacuum-sealed flanges and other various connectors can be implemented to provide multiple vacuum sealable and re-sealable points of access to the housing. By way of example only, the flange 114 can be affixed to the outer surface of the cube-shaped housing 104 using threaded fasteners, such as nuts and bolts or screws.

According to an exemplary embodiment, the flange 114 is a rotatable flange. With a rotatable flange, the bolt pattern is defined by an outer part of the flange, and an inner part of the flange can rotate with respect to this outer part. Regular flanges are generally made of one piece of metal, with a defined bolt pattern, and can only be rotated in increments defined by the frequency of the bolt holes that are available on the vacuum assembly. By contrast, a rotatable flange allows an arbitrary amount of rotation, which is useful for positioning the sample. The inner part of the rotatable flange can rotate, while the outer part stays fixed. Accordingly, handles 126 are provided to allow a user to rotate the inner part of the flange relative to the outer part (e.g., one handle is affixed to the inner part of the rotatable flange 114 and another handle is attached to the outer part of the rotatable flange 114. See also FIG. 5, described below. By rotating flange 114, the user can thereby rotate rod 116 and sample mounting structure 120 attached to rod 116, as well the heating element 122 and transparent (e.g., quartz) carrier 124 (having the sample) which are attached to the sample mounting structure 120. See above. This permits the user to rotate the sample to achieve good alignment with the spectrometer light beam. Rotatable flanges are commercially available, for example, from the Kurt J. Lesker Company®, Clairton, Pa. Use of the rotating flange in the present spectrometer insert 102 to adjust the position of the sample mounting and heating assembly is further illustrated in FIG. 2.

Figure 2:
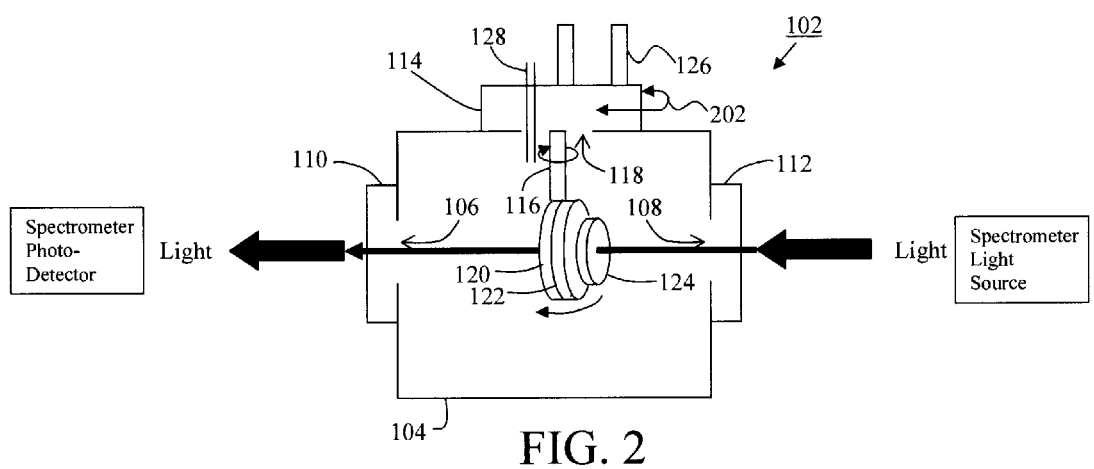
FIG. 2 is a cross-sectional diagram illustrating use of a rotating flange to adjust a positioning of a sample mounting and heating assembly of the present spectrometer insert according to an embodiment of the present invention.

Specifically, as shown in FIG. 2, by turning/rotating the flange 114, the sample mounting and heating assembly (i.e., the sample mounting structure 120, the heating element 122, and transparent (e.g., quartz) carrier 124 (having the sample)—which are all ultimately attached to the flange 114 via the rod 116) will rotate. This action will adjust the positioning of the sample mounting and heating assembly within the path of the spectrometer light beam. Preferably, the flange can be rotated in a clockwise or counterclockwise direction (see arrows 202) which corresponds to a same clockwise or counterclockwise adjustment of the sample mounting and heating assembly within the cube-shaped housing 104. For illustrating purposes only, in the example illustrated in FIG. 2, the flange 114 has been rotated in a clockwise direction, resulting in a clockwise adjustment of the sample mounting and heating assembly.

Referring back to FIG. 1, as highlighted above, the present spectrometer insert permits operation under vacuum. Thus a pumping port 128 is provided to permit a vacuum to be applied to the interior of the cube-shaped housing 104. According to an exemplary embodiment, the pumping port includes a one-way valve configured to attach to a vacuum pump. In the exemplary embodiment shown illustrated in FIG. 1, the pumping port is located in the flange 114. The flange is a convenient location for the pumping port for several reasons. First, since the flange 114 is preferably easily removable from the cube-shaped housing 104, swapping out a defective pumping port involves dealing with only the flange 114 rather than the cube-shaped housing 104. Second, to reduce the overall complexity of the cube-shaped housing 104, a modular design is preferably employed wherein generic (i.e., any one of the ports in the housing can be used for any of the components described herein), same sized ports are provided on each side of the cube. Thus, the cube can then be configured in a variety of ways by affixing the desired components (windows, flanges, etc.) to any of the respective ports. By locating the pumping port in the flange 114 (rather than in the cube-shaped housing 104 itself), the modular nature of the cube-shaped housing 104 can be maintained (i.e., placing the pumping port in the housing itself would, by comparison, dictate a particular orientation of the cube-shaped housing 104 based on the location of the pumping port).

According to an exemplary embodiment, the cube-shaped housing 104 is formed from a corrosion resistant metal, such as stainless steel. It is notable that while the figures depict the housing to be a cube (i.e., a structure having six sides) this is merely one exemplary configuration, and other configurations of the enclosed housing are possible. By way of example only, the housing 104 may instead have a rounded, cylindrical, and/or spherical shape. Basically, any enclosed (vacuum chamber) housing shape may be employed in the same manner as described herein as long as ports and flanges can be provided in the same manner and configuration as described. As shown in FIG. 1, the cube-shaped housing 104 is hollow such that the (first, second, etc.) sides thereof define an enclosed inner cavity of the cube-shaped housing 104 into which the sample is introduced (and heated), and through which the spectrometer light beam passes (via window openings 106 and 108, and transparent windows 110 and 112, respectively).

The present insert is intended for use with conventional benchtop spectrometers. In general, a spectrometer has a light source and a photodetector (a photosensor). The photodetector is used to measure an intensity of light (generated by the light source) which is transmitted from a sample. During operation, when the sample is encased in spectrometer insert 102 and the spectrometer insert 102 is inserted in a benchtop spectrometer, the spectrometer light source shines light through transparent window 112 and window opening 108 of the insert 102. Light is then incident on the sample and is either absorbed, reflected, or transmitted. The transmitted light is then passed through a hole in the heating element 122, through a hole in the sample mounting structure 120, through the window opening 106 and transparent window 110, and is finally incident on the spectrometer photodetector. See FIG. 1.

The various components of the present spectrometer insert 102 will now be described in further detail. FIG. 3, for example, illustrates an exemplary configuration of the transparent windows 110 and 112 covering the first and second window openings 106 and 108, respectively, in the opposing first and second sides of the cube-shaped housing 104. It is notable that in the following figures the details regarding the components and structures related to a particular side or sides of the cube-shaped housing 104 will be illustrated, while components pertaining to other regions or sides of the housing are not shown. This is done for clarity to illustrate the details of each set of components individually, and is not intended to imply that the components and structures related to other sides of the cube-shaped housing 104 are not or will not be present. This also highlights the modular nature of the housing design wherein the various components described herein can be added to the sides of the housing in any order, and in various different configurations (for example, the components described herein do not necessarily have to be mated to the particular side of the housing as described in the examples herein).

Figure 3:
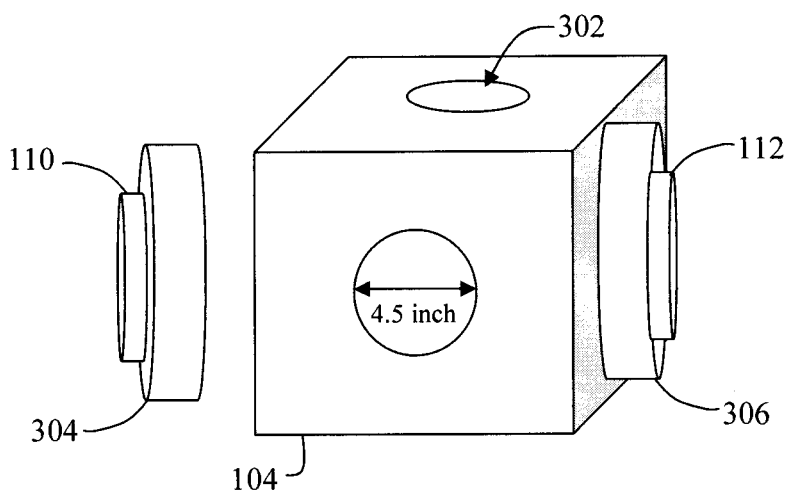
FIG. 3 is a three-dimensional diagram illustrating an exemplary configuration of transparent windows covering window openings in opposing sides of the present spectrometer insert according to an embodiment of the present invention.

In the example illustrated in FIG. 3, the cube-shaped housing 104 includes a port 302 in each of its (six) sides. It is these ports 302 in the opposing first and second sides of the cube-shaped housing 104 that make up the first and second window openings 106 and 108, respectively. As provided above, the cube-shaped housing 104 is a hollow metal (e.g., stainless steel) cube structure. The ports 302 are openings to the interior of the cube structure. As highlighted above, generic (i.e., any one of the ports 302 in the housing can be used for any of the components described herein), same sized ports are provided on each side of the cube the cube-shaped housing 104. As shown in FIG. 3, each of the ports 302 is preferably centrally located in its respective side of the housing. Centrally locating ports 302 is advantageous to insuring that the various components of the insert are properly aligned (both with one another and with the spectrometer components). For instance, placing the transparent windows 110 and 112 over centrally located window openings 106 and 108 (which are both ports 302 in the housing) insures that the transparent windows 110 and 112 are within line-of-sight with one another, and within the path of the spectrometer light beam from light source to photodetector. Placing the sample centrally within the interior of the housing then also insures that the sample is within the path of the light beam.

It is preferable that the present spectrometer insert permits operation under vacuum. Accordingly, the ports 302 may be configured with vacuum seals or connections. By way of example only, each of the ports 302 may be fitted with vacuum flanges. One suitable type of vacuum flange includes a conflat (CF) configuration wherein a copper gasket between opposing flanges forms an air-tight seal.

According to an exemplary embodiment, the transparent windows 110 and 112 are formed from a commercially available sapphire or deep-UV quartz material. Conflat flanged glass viewing ports are commercially available, including those fitted with sapphire or deep-UV quartz windows. It is notable that the cost of these specialized windows scales with their size. Thus, in the interest of cost savings, a smaller window fitting is preferred. Zero-length adapters 304 and 306 can be used to mate smaller windows 110 and 112, respectively, to larger ports 302, if necessary. Conflat flanged zero-length adapters are commercially available.

For instance, if the ports 302 in the cube-shaped housing 104 have a 4.5 inch diameter (see FIG. 3) and 2.75 inch windows are chosen to minimize the cost of the assembly (i.e., 2.75 inch windows are less costly than 4.5 inch windows), then commercially available (4.5 inch to 2.75 inch) zero-length adapters can be used to allow the smaller windows to be connected to the larger ports. Ports of any dimension would accomplish the same function. As provided above, to reduce the overall complexity of the cube-shaped housing 104, a modular design is preferably employed wherein generic, same sized ports are provided on each side of the cube. Thus ports 302 of a certain minimum size are needed (e.g., to introduce the heating element, sample mounting structure, etc. into the housing) which may be larger than necessary for the windows 110 and 112. The use of zero-length adapters can serve to mate the smaller windows to the larger ports, and thus realize a cost savings.

Figure 4:
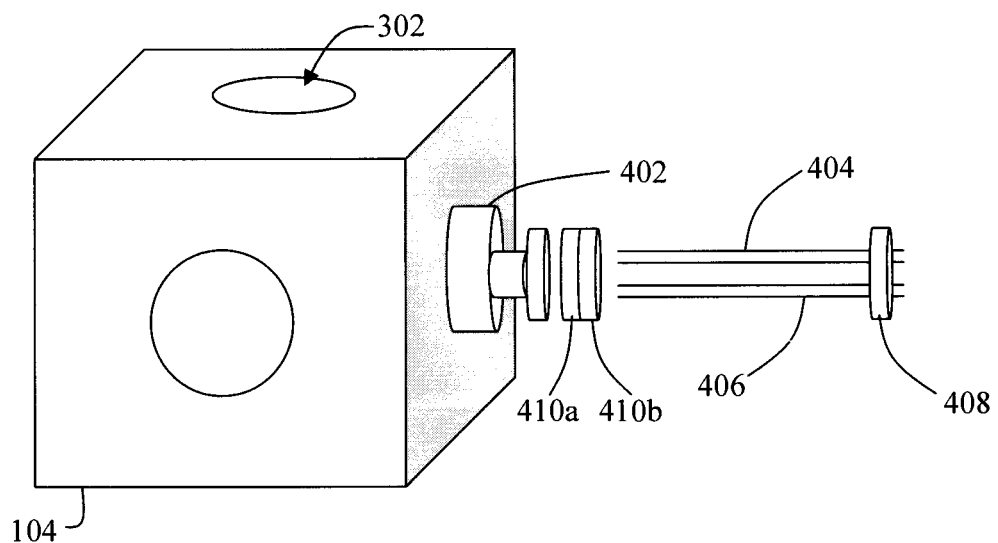
FIG. 4 is a three-dimensional diagram illustrating an exemplary configuration of heating wires for connecting a heating element to a power supply, and a thermocouple for measuring sample temperature which are provided through a port in a fourth side of the present spectrometer insert according to an embodiment of the present invention.

FIG. 4 illustrates an exemplary configuration of the heating wires for connecting the heating element 122 to a power supply, and the thermocouple for measuring sample temperature which are provided through a port in the third side of the cube-shaped housing 104. As described above, in this exemplary configuration the third side of the cube-shaped housing 104 is perpendicular to the first side (having window opening 106 and transparent window 110), the second side (having window opening 108 and transparent window 112), and the fourth side (having opening 118 through which the sample, sample holder and heating element are introduced into the insert) of the cube-shaped housing 104.

In the example shown in FIG. 4, a flange 402 is provided on the cube-shaped housing 104 through a port 302 in the third side of the housing. By way of example only, the flange 402 is a straight, reducing vacuum flange (i.e., reducing the flange size from that of the port 302 to that of the fitting through which the heater wires and thermocouple pass), and more particularly a conflat straight, reducing flange.

Specifically, the heating element(s) used in the insert (such as heating element 122) is/are connected to a standard power supply (not shown) via a wire(s) 404. Feedback regarding the temperature of the sample (and potentially the temperature of one or more other regions and areas of the insert) may be provided by way of thermocouple leads 406. As shown in FIG. 4, the heating wires 404 and the thermocouple leads 406 pass through a flat flange 408. In order to insure a vacuum seal, the heating wires 404 and the thermocouple leads 406 are sealed to the flat flange 408, such that when the flat flange 408 is connected to the flange 402 the heating wires 404 and the thermocouple leads 406 pass (via the flat flange 408) from the interior cavity of the housing to outside the housing. As highlighted above, the flange 402 may be a reducing flange. This optional feature may be employed to reduce the size of the flat flange 408 needed, thereby reducing production costs (see above).

As further illustrated in FIG. 4, since the heating wires 404 and the thermocouple leads 406 are sealed to the flat flange 408, their length is fixed. Thus, when the flat flange 408 is connected to the flange 402 a fixed length of the heating wires 404 and the thermocouple leads 406 pass into the interior cavity of the housing. When sealing the heating wires 404 and the thermocouple leads 406 to the flat flange 408, an approximation may be made as to the length of the wires and leads needed within the cavity. One or more spacers 410a, 410b, etc. may be employed between the flange 402 and the flat flange 408 to vary the distance by which the heating wires 404 and the thermocouple leads 406 extend into the interior cavity of the housing. The notion here is that an excess length of wire in the cavity might bunch up and interfere with the optical measurement. Thus, it is preferable to have only the length of wire needed present in the interior cavity of the housing, which can be achieved using the spacers 410a, b, etc.

As is known in the art, a thermocouple is a temperature measuring device that produces a voltage in response to changes in temperature. Depending on thermocouple type (e.g., type K, type C, type R, etc.) an appropriate material combination can be selected which will be resilient to the needed temperature changes and provide reliable readings at the desired temperatures. In the context of the present techniques, the thermocouple leads 406 can be placed proximal to the heating element 122, the sample, and/or one or more other locations in the housing to record the temperature. This allows feedback such that the temperature can be monitored and controlled as desired. A thermally conductive cement may be employed to make good thermal contact between the thermocouple and an area of interest (and has the added benefit of keeping everything in place). Omega Engineering, Stamford, Conn., for example, produces cement-on surface thermocouples. Multiple heating elements and/or thermocouples may be employed. For instance, multiple thermocouples may be used to monitor the surface temperature of the heating element 122, the sample, and/or the inner walls of the interior cavity of the housing.

Figure 5:
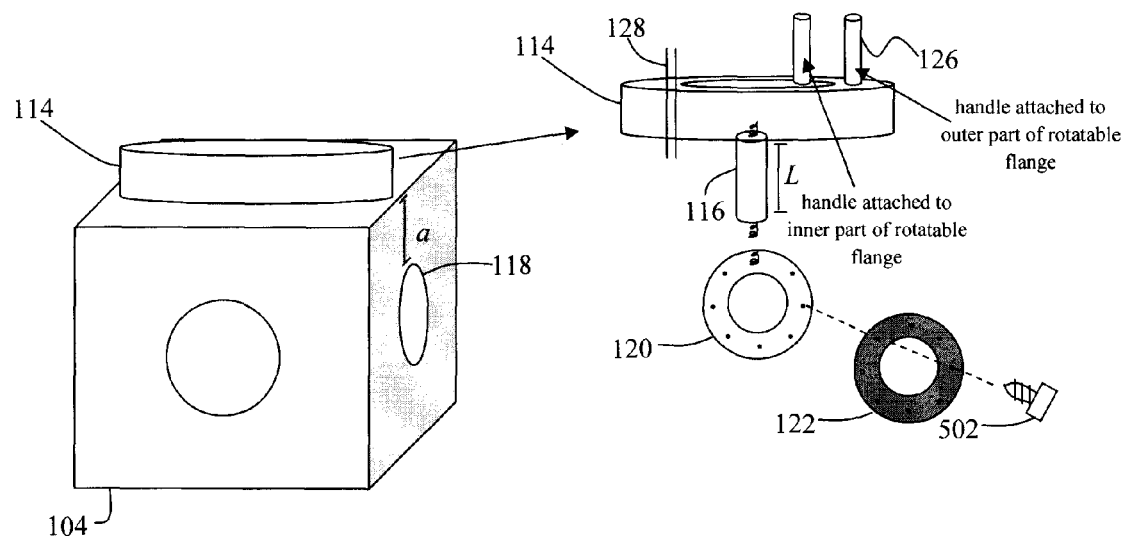
FIG. 5 is a three-dimensional diagram illustrating an exemplary configuration of a flange (affixed to the outer surface of the fourth side of the cube-shaped housing) to which the sample mounting and heating assembly is attached according to an embodiment of the present invention.

FIG. 5 illustrates an exemplary configuration of the flange 114 (affixed to the outer surface of the fourth side of the cube-shaped housing 104) to which the sample mounting and heating assembly is attached. As described above, in this exemplary configuration the fourth side of the cube-shaped housing 104 is perpendicular to the first side (having window opening 106 and transparent window 110), the second side (having window opening 108 and transparent window 112), and the third side (through which the heating wires and thermocouple leads are introduced) of the enclosed cube-shaped housing 104.

Specifically, in the exemplary embodiment shown in FIG. 5, the sample mounting structure 120 is attached to the flange 114 by the (electrically insulating) rod 116. The rod 116 is of a length that when the flange 114 is connected to the outer surface of the fourth side of the cube-shaped housing 104 the sample mounting structure 120 extends a certain distance into the inner cavity of the housing. Since the sample mounting structure 120 will be used to mount the heating element and the transparent (e.g., quartz) carrier 124 (not shown in FIG. 5) with the sample, the length L of rod 116 is preferably equal to a distance a from an outer surface of the fourth side of the cube-shaped housing 104 to a top of the window opening 118. See FIG. 5. This will position the sample mounting structure 102 in line with window openings 106 and 108, through which the spectrometer light beam will pass.

According to an exemplary embodiment, the rod 116 and the sample mounting structure 102 are formed from a heat-resistant, ceramic material, such as MACOR. MACOR is a machineable glass ceramic material available from Corning, Inc, Corning, N.Y. FIG. 5 further illustrates the above-described exemplary configuration wherein the sample mounting structure 120 (and the heating element 122) are formed in the shape of a disc having a hole in its center for light penetration. The sample mounting structure 120 and the heating element 122 may also be geometrically matched to one another (e.g., the sample mounting structure 120 and the heating element 122 are configured to have the same sized disc-shaped structure). In the example shown in FIG. 5, the sample mounting structure 120 and the heating element 122 have aligned holes therein through which fasteners (e.g., screws 502) can be used to mount the heating element 122 to the sample mounting structure 120. Other fastening methods, such as clips, hooks, etc. may also be used. For instance, one or more clips may be placed around the perimeter of the sample mounting structure 120 and the heating element 122 to secure the two components together.

According to an exemplary embodiment, the heating element 122 is a graphite heating element. Graphite heating elements are well suited for vacuum environments, and can be produced in any number of shapes and sizes. Other types of heating elements are also possible. For instance, according to another exemplary embodiment, a metal foil heater is used. Metal foil heaters are extremely thin (e.g., the metal foil can be as thin as 12 micrometers) and can be patterned into a variety of shapes using standard techniques. By way of example only, a tantalum or tungsten foil heater performs well in accordance with the present techniques. Advantageously, tantalum or tungsten foil heaters are sensitive to the environment. However, use of a metal foil heater requires having good vacuum to prevent the foil from oxidizing during heating. In the example shown in FIG. 5, the heating element 122 is formed as a disc-shaped structure geometrically matched to the sample mounting structure. Other heating element shapes are also possible, see above. The heating wires 404 (see above) can be used to connect the heating element to a power supply thereby permitting heating of the sample within the housing. As highlighted above, multiple heating elements and/or thermocouples may be employed.

As highlighted above, the flange 114 may be a rotatable flange, wherein by rotating the flange 114, a user can thereby rotate rod 116 and sample mounting structure 120 attached to rod 116, as well the heating element 122 and transparent (e.g., quartz) carrier 124 (having the sample) which are attached to the sample mounting structure 120. Accordingly, (two) handles 126 may be included to assist in rotating the flange 114. As highlighted above, a pumping port 128 may be provided in flange 114 to permit a vacuum to be applied to the interior of the cube-shaped housing 104. See FIG. 5.

Figure 6:
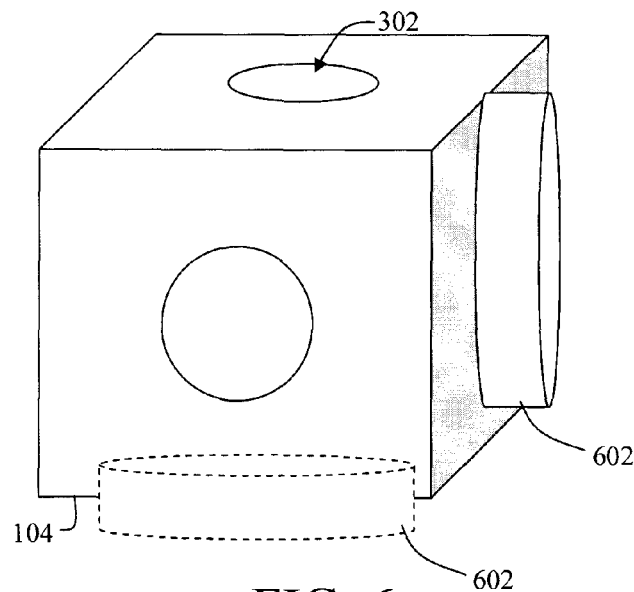
FIG. 6 is a three-dimensional diagram illustrating ports being blocked off with a blank flange (to block off an unused port) or a flange through which additional features could be introduced to the assembly according to an embodiment of the present invention.

As provided above, according to an exemplary embodiment the cube-shaped housing 104 has a modular design wherein generic (i.e., any one of the ports 302 in the housing can be used for any of the components described herein), same sized ports 302 are provided on each side of the cube. Thus, in some configurations of the insert, one or more of the ports are unused and may be blocked off. For instance, if the only requirements are temperature-dependent optical measurements under vacuum conditions, then any additional ports may be unused. See FIG. 6. Specifically, in the exemplary configuration depicted in the figures, the ports 302 in the fifth and sixth sides of the cube-shaped housing 104 are not being used. As shown in FIG. 6, these unused ports may be blocked off with a blank flange 602. According to an exemplary embodiment, the blank flange(s) 602 are conflat flanges.

However, if there are other experimental requirements, for example gradient-heating/cooling or ambient-environment gas composition control, then these other ports could be used to provide these experimental conditions. For instance, other features may be introduced to the assembly through these ports to probe their effects on optical properties of the sample (i.e., along with temperature), e.g., as a function of gas ambient (these flanges can be used to flow in a gas or gasses which could interact with the sample at elevated temperatures, to probe the effect on optical properties of the sample).

Figure 7:
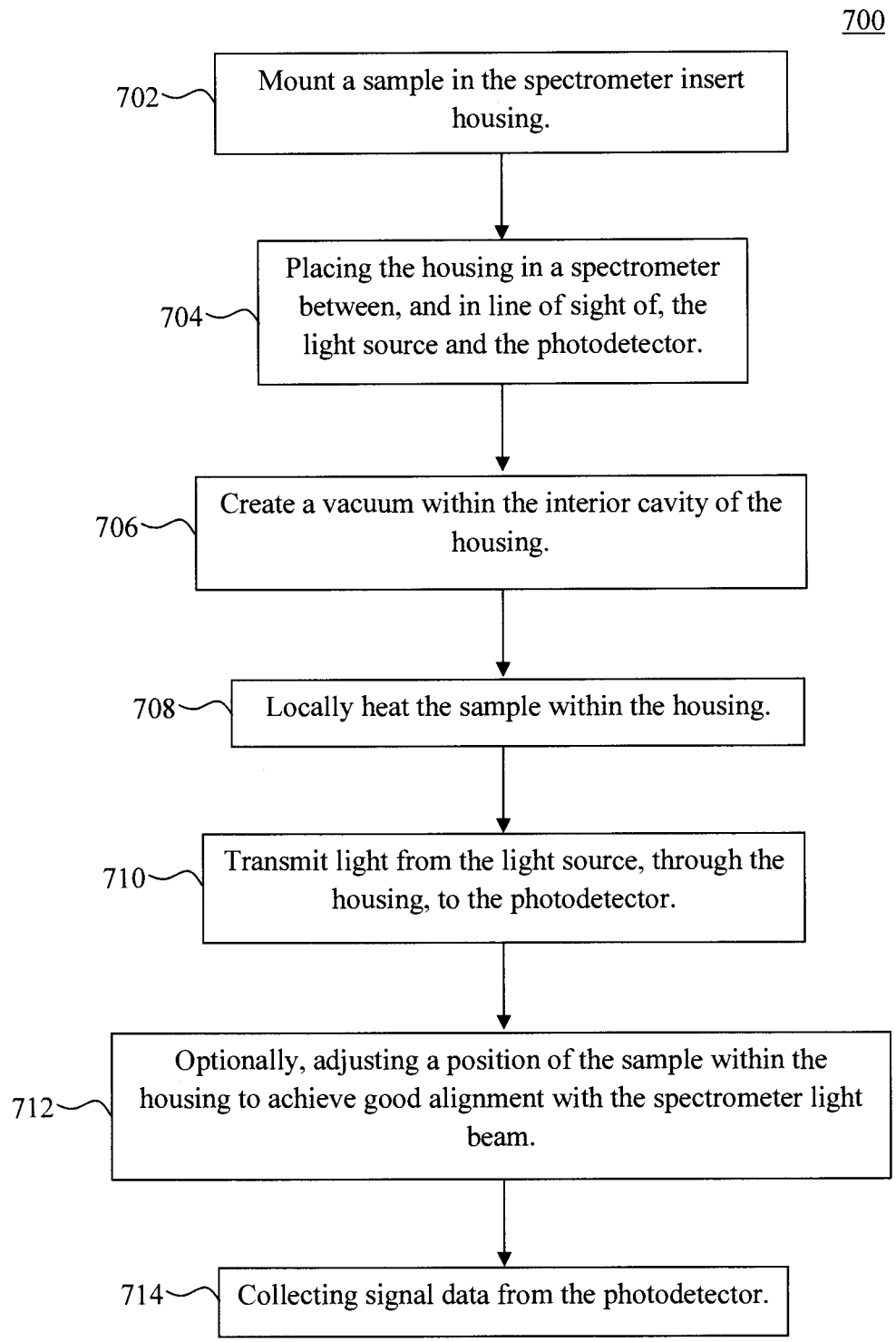
FIG. 7 is a diagram illustrating an exemplary methodology for using the present spectrometer insert to analyze a sample according to an embodiment of the present invention.

Given the above description of the present spectrometer insert design, an exemplary methodology for using the insert to analyze a sample is now provided by way of reference to methodology 700 of FIG. 7. In step 702, a sample is inserted into the cube-shaped housing 104. As described above, the sample may be placed, deposited, etc. on a transparent (e.g., quartz) carrier 124 which is then mounted to the heating element 122. The sample and heating element are positioned in the center of the interior cavity of the cube-shaped housing 104 via the sample mounting structure 120 and (electrically insulating) rod 116. See above. In one non-limiting exemplary implementation, the sample mounting and heating assembly is assembled by taking the transparent (e.g., quartz) carrier 124, laying the (e.g., tantalum or tungsten metal foil) heating element 122 onto the transparent carrier (with a hole in the center of the heating element to transmit light), laying the sample on top of the transparent carrier 124, and then clipping the whole stack onto the (disc-shaped) sample mounting structure 120 using the holes drilled into the disc.

By way of example only, the present spectrometer insert is ideal for measuring the temperature-dependent optical properties of a semiconductor material, which can be used to analyze the performance of the material at elevated temperatures. A given semiconductor sample of interest can be deposited onto the transparent (e.g., quartz) carrier 124, and the sample/transparent carrier 124 can be mounted onto the sample mounting and heating assembly as described above.

In step 704, the insert having the above-described components and the sample mounted therein, is then placed within a spectrometer. As described above, the insert is positioned in the spectrometer between the spectrometer light source and the spectrometer photodetector such that the transparent windows 110 and 112 are within line of sight of the light source and the photodetector (i.e., during operation, light from the light source may pass through transparent windows 110 and 112 to the photodetector).

In step 706, a vacuum is created within the insert. As described above, the components of the insert are assembled so as to provide an airtight seal, permitting a vacuum to be drawn in the interior cavity of the cube-shaped housing 104. A vacuum can be created within cube-shaped housing 104 by attaching the pumping port 128 to a vacuum pump.

There are a few main reasons why having a vacuum is useful: (1) when a metal (e.g., tantalum or tungsten) foil heating element is employed, having a vacuum prevents the metal (e.g., tantalum or tungsten) foil heating element from oxidizing—there is no oxygen to interact with the metal (e.g., tantalum or tungsten); (2) having a vacuum prevents convective heat transfer between the sample+heater to the outer walls of the metal housing (which reduces power consumption for heating the sample, and also prevents the whole metal housing from getting hot—a safety hazard); and (3) having a vacuum prevents the sealed assembly from pressurizing (as would happen at atmosphere if room-temperature gasses were allowed to heat up inside an enclosed vessel). According to an exemplary embodiment, a base pressure of $1 \times 10^{-7}$ Torr is employed.

In step 708, the sample is heated via the heating element 122. In order to measure the temperature-dependent optical properties of the sample, it may be desirable to analyze the sample at a range of temperatures (i.e., at multiple temperatures). Since the heating element 122 is present on the sample mounting and heating assembly proximal to the sample, local heating of the sample can be achieved. This prevents potential heat damage to the spectrometer from occurring. Further, the cube-shaped housing 104 itself provides a physical barrier between the heated sample and the spectrometer. No such barrier would be present if a heated sample was placed directly in the device.

As described above, the heating element is connected to a power supply by the heating wires 404. A thermocouple is used to monitor the temperature of the sample. Multiple heating elements and/or thermocouples may be employed to heat/monitor the surface temperature of the sample, the walls of the housing, etc.

In step 710, light from the spectrometer light source is passed through the cube-shaped housing 104 (via transparent windows 110 and 112). Light incident on the sample is either absorbed, reflected, or transmitted. The transmitted light is then incident on the spectrometer photodetector. In the exemplary configuration described above wherein a disc-shaped heating element 122 and mounting structure 120 are employed, the spectrometer light beam passes through the hole in the center of the heating element 122 and through the hole in the center of the sample mounting structure 120.

Optionally, in step 712, when the sample mounting and heating assembly are affixed to the cube-shaped housing 104 via a rotating flange, the position of the sample mounting and heating assembly within the interior cavity of the housing can be adjusted (by turning the rotating flange—see FIG. 2) to achieve good alignment with the spectrometer light beam. For instance, the sample mounting and heating assembly can be placed inside the spectrometer. Most commercial software packages have an alignment feature with feedback where you can see how much light is transmitted as you adjust the position of your sample in the tool. The alignment can then be adjusted (e.g., via the rotating flange) to make sure it is optimized. Alternatively, one can "eyeball" it, and then just rotate the whole housing/assembly inside of the spectrometer to accomplish alignment.

In step 714, signal data is collected from the photodetector. This data represents the optical properties (e.g., absorbance) of the sample at the temperatures tested. For instance, the collected data can be used to assess how the optical properties of the sample change as the temperature of the sample is increased (i.e., the temperature-dependent optical properties of the sample).

Figure 8:
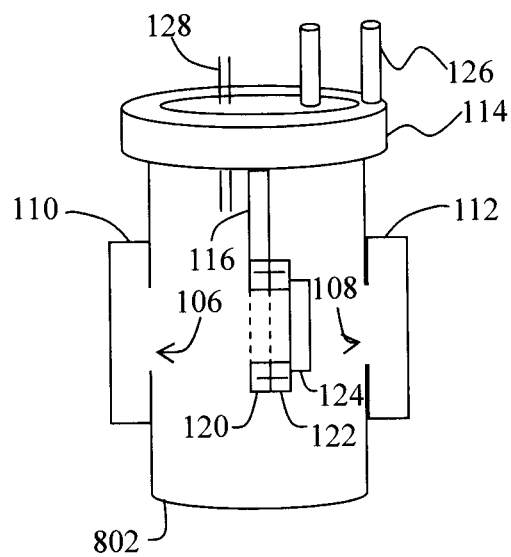
FIG. 8 is a diagram illustrating an exemplary configuration of the present spectrometer insert having a cylindrical housing according to an embodiment of the present invention.
Figure 9:
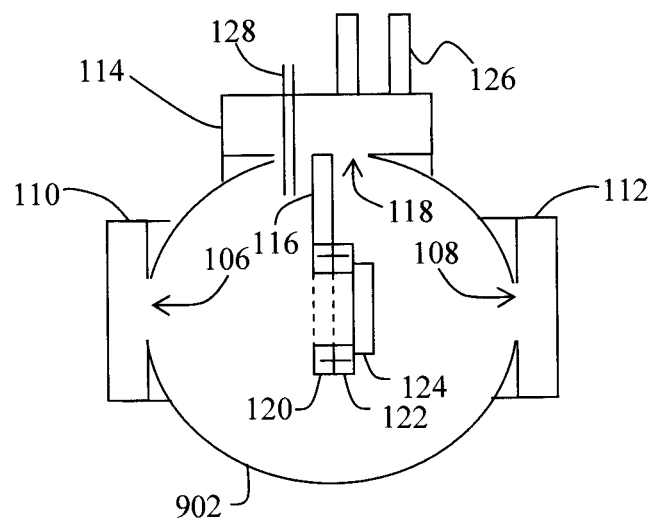
FIG. 9 is a diagram illustrating an exemplary configuration of the present spectrometer insert having a spherical housing according to an embodiment of the present invention.

As described above, a cube-shaped housing is only an exemplary configuration of the present insert housing. In fact, any housing shape may be employed as long as ports and flanges can be provided in the same manner and configuration as described above. By way of example only, a cylindrical housing 802 is shown in FIG. 8 and a spherical housing 902 is shown in FIG. 9. Since the same components would be assembled to the housing in the same manner regardless of the shape of the housing, the above-described components (such as the sample mounting and heating assembly, transparent windows, etc.) are also numbered alike in FIGS. 8 and 9. In the context of a cylindrical, spherical, etc. housing reference above to the first, the second, etc. sides of the housing are understood to refer to specific surfaces of the housing since cylinders and spheres generally do not have 'sides.' Thus, for instance, as would be apparent to one skilled in the art given the present teachings, when reference is made to opposing 'sides' of the housing this is intended to mean opposing 'surfaces' of the housing in the case of a cylindrical or spherical housing. See, for example, FIGS. 8 and 9 wherein transparent windows 110 and 112 are located on opposing surfaces of the cylindrical or spherical housing, respectively, in line of sight of one another.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method for analyzing temperature-dependent optical properties of a sample, comprising the steps of:
    mounting the sample in a spectrometer insert, wherein the spectrometer insert comprises i) an enclosed housing, ii) a first transparent window on a first outer side of the enclosed housing, iii) a second transparent window on a second outer side of the enclosed housing, wherein the first outer side and the second outer side are opposing sides of the enclosed housing, such that light can pass completely through the enclosed housing via the first transparent window and the second transparent window, and iv) a sample mounting and heating assembly connected to a flange on a fourth outer side of the enclosed housing, to which the sample is mounted, positioned within an interior cavity of the enclosed housing in between, and in line of sight of, the first transparent window and the second transparent window, and wherein the sample mounting and heating assembly is connected to the flange via an electrically insulating rod, the electrically insulating rod having a length configured to position the sample mounting and heating assembly within the interior cavity of the enclosed housing in between, and in line of sight of, the first transparent window and the second transparent window;
    placing the spectrometer insert in a spectrometer such that the spectrometer insert is between a light source of the spectrometer and a photodetector of the spectrometer, wherein the light source and the photodetector are external to the enclosed housing, and wherein the first transparent window and second transparent window are within line of sight of the light source and the photodetector;
    creating a vacuum within the enclosed housing;
    heating the sample to one or more temperatures;
    transmitting light from the light source, through the enclosed housing via the first transparent window and the second transparent window, to the photodetector; and
    collecting data from the photodetector relating to optical properties of the sample at the one or more temperatures.

2. The method of claim 1, wherein the sample mounting and heating assembly comprises a sample mounting structure, and a heating element attached to the sample mounting structure, wherein the sample is deposited onto a transparent carrier, and wherein the transparent carrier is mounted to the heating element.

3. The method of claim 2, wherein the sample is heated via the heating element.

4. The method of claim 1, wherein the flange is a rotating flange, the method further comprising the step of:
    adjusting a position of the sample mounting and heating assembly within the interior cavity of the enclosed housing by turning the rotating flange.

5. The method of claim 1, wherein thermocouple leads are introduced into the interior cavity of the enclosed housing through a port in a third outer side of the enclosed housing, the method comprising the step of:
    monitoring a surface temperature of the sample using the thermocouple leads.

\* \* \* \* \*